United States Patent [19]

Ouchi et al.

[11] Patent Number: 4,461,282
[45] Date of Patent: Jul. 24, 1984

[54] MECHANISM FOR DIRECTION CHANGING OF ENDOSCOPE TOP END

[75] Inventors: Teruo Ouchi; Kiyoshi Chikashige, both of Saitama, Japan

[73] Assignee: Kabushiki Kaisha Medos Kenkyusho, Tokyo, Japan

[21] Appl. No.: 35,183

[22] Filed: May 2, 1979

[30] Foreign Application Priority Data

May 2, 1978 [JP] Japan .................. 53-53093

[51] Int. Cl.$^3$ .............................. A61B 1/00
[52] U.S. Cl. ......................................... 128/4
[58] Field of Search ........................... 128/3-8, 128/DIG. 9; 356/241; 350/96, 26; 188/74, 325, 326; 192/71, 75, 76

[56] References Cited

U.S. PATENT DOCUMENTS

| | | | |
|---|---|---|---|
| 3,557,780 | 1/1971 | Sato | 128/4 |
| 3,788,303 | 1/1974 | Hall | 128/4 |
| 3,897,775 | 8/1975 | Furihata | 128/6 |
| 4,078,555 | 3/1978 | Takahashi | 128/4 |

Primary Examiner—Michael H. Thaler
Attorney, Agent, or Firm—Sughrue, Mion, Zinn, Macpeak and Seas

[57] ABSTRACT

A device for changing a direction of the top end part of an endoscope in which a manual operating section is coupled to a top end part curving section through wires and the top end part curving section is curved vertically and horizontally by pulling the wires. A pair of wires are adapted to drive the top end part curving section vertically and horizontally, respectively, and a pair of drive members pull the wires directly or through intermediate members. Rotating knobs are integrally coupled to the pair of drive members so as to control the top end part curving section vertically and horizontally. A pair of brake drums confront one another, and a frictional member or brake shoe is mounted on a stationary member of the device in such a manner that it is movable with respect to the pair of brake drums. An external operating lever controls the movement of the brake shoe and the brake shoe abuts against the pair of brake drums by operation of the external operating lever so that simultaneous braking occurs.

9 Claims, 6 Drawing Figures

MECHANISM FOR DIRECTION CHANGING OF ENDOSCOPE TOP END

BACKGROUND OF THE INVENTION

This invention relates to a device for operating the top end part curving section of an endoscope. A specific aspect of the invention resides in a braking mechanism which is operated under the condition where the direction of the top end part of the endoscope has been determined, and is to be maintained.

In order to observe a portion of a body cavity or to take a picture thereof, the top end part having an observing window of an endoscope is inserted thereinto. In this case, it is necessary to frequently change the direction of the top end part of the endoscope in order to sufficiently observe the portion of the body cavity. For this purpose, in an endoscope of this type, a top end part curving section which is very flexible is provided between the top end part and a flexible pipe coupling the top end part to the manual operating section of the endoscope. The top end part curving section is curved vertically and/or horizontally by strings which are pulled by the manual operation section.

With such a curving section operating mechanism, the portion to be examined is located through observation of the body cavity to take a picture thereof or to perform an operation with forceps or the like. If, in this case, it is possible to maintain the condition of the curving section and accordingly the direction of the top end part of the endoscope as it positioned relative to the affected area, then it is efficient and convenient in conducting subsequent procedures. Accordingly, the curving section operating mechanism is provided with a brake mechanism.

Employed as the brake mechanism in such endoscopes are a pair of rotating knobs curving the which curve section vertically and horizontally, respectively, --; and which is supported in parallel with each other by supporting members. The supporting members are simultaneously clamped and held by applying clamping pressure in the axial directions of the supporting members. Levers are provided for vertically and horizontally operating units, respectively, and these operating units are separately clamped and held by the levers. A braking system of this type has been put to practical use.

In the actual operation of the endoscope for locating the affected part in the body cavity, the vertical and horizontal curving operations are alternately carried out to orientate the top end part of the endoscope as desired. In this operation, it is necesaary to finely adjust the direction of the top end part vertically and/or horizontally even after the top end part has been directed to the affected part in the body cavity.

In the clamping structure in the axial direction of the supporting members, in the above-described conventional mechanism, the clamping part is in the central region around the supporting shaft of the rotating knob. Therefore the supporting members cannot be clamped and held without increasing the clamping pressures. If the clamping pressures are increased, then it is difficult to finely adjust the direction of the top end part of the endoscope by turning the operating knob under pressure of the braking action. Thus, in the conventional mechanism, it is difficult to design the construction of the frictional surface for applying a suitable brake force and to adjust the clamping pressure.

In the conventional mechanism for separately holding the knobs operating to curve the curving section respectively vertically and horizontally, application of brake forces to the operating knobs to hold them, and release of the applied brake forces must be carried out alternately in locating the affected part in the body cavity and in finely adjusting the direction of the top end part of the endoscope. This is undoubtedly troublesome and prolongs the surgical procedure.

SUMMARY OF THE INVENTION

Accordingly, an object of this invention is to provide a device for changing the direction of the top end part of an endoscope, in which operating mechanism for changing the direction of the top end part vertically and horizontally are provided with brake drum type mechanisms having frictional surfaces in the peripheral regions of the operating knobs thereof, and a part of a brake mechanism is commonly used for these operating mechanisms to simultaneously apply a suitable brake force to the latter.

It is another object of this invention to eliminate all of the above-described drawbacks accompanying a conventional mechanism.

Yet another object of the invention resides in the technique of maintaining the operating mechanisms a in condition braked, wherein they may be separately released from the braking actions, when necessary, to thereby facilitate the affected part locating operation and the fine adjustment of the direction of the top end part of the endoscope.

This invention will be described in detail with respect to its preferred embodiment shown in the accompanying drawings.

DESCRIPTION OF THE PREFERRED EMBODIMENTS

Figure 1:
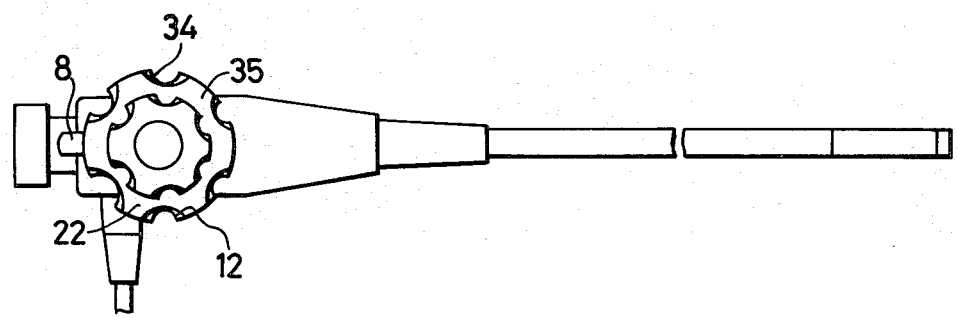
FIG. 1 is a diagram showing the external appearance of a device for changing the direction of the top end part of an endoscope, according to this invention.
Figure 2:
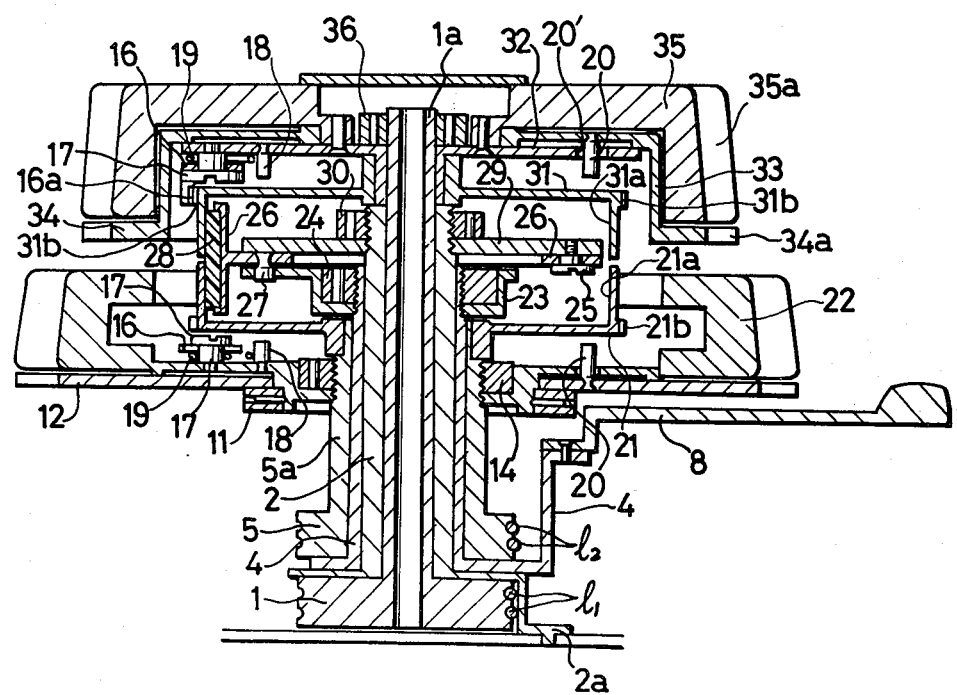
FIG. 2 is a sectional view showing the essential components of the device according to the invention.

FIG. 1 shows the external appearance of an endoscope having a curving device according to the invention. FIG. 2 is a vertical sectional view showing the essential components of the curving device. A pulling string $l_1$ for curving (horizontally) the top end part of the endoscope is wound on a drum 1. A shaft 1a is extended from the drum 1. An operating knob 35 is fixedly secured to one end portion of the shaft 1a by fixing the central engaging member of a rotating plate 32 integral with the operating knob 35 by means of a fixing member 36, so that the drum 1 can be rotated by rotating the knob 35 with the finger or the like.

Figure 3:
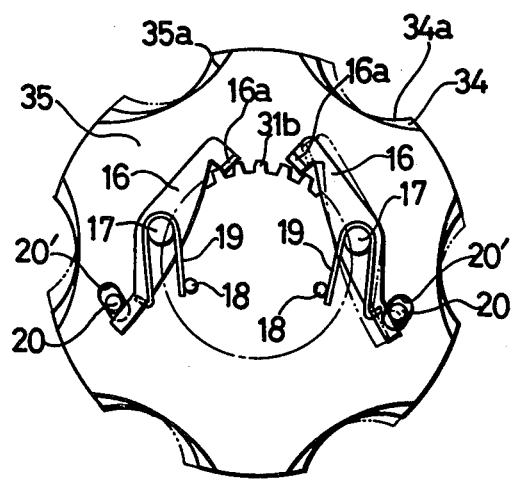
FIG. 3 is a plan view showing the clutch mechanism of the device shown in FIG. 2.

The periphery of the operating knob 35 is partly cut to form finger placing recesses 35a as shown in FIG. 3.

The operating knob 35 is provided with an auxiliary knob 34 the periphery of which is also partly cut to form finger placing recesses 34a as indicated by the dotted lines in FIG. 3. As is apparent from FIG. 3, the amount of cut in the auxiliary knob 34 is less than that in the operating knob 35. These knobs 35 and 34 are coaxially fitted over the aforementioned shaft 1a, and pins 20 embedded in the auxiliary knob 34 engage with elongated grooves 20' in the rotating plate 32 integral with the operating knob 35, so that the finger placing recesses 35a and 34a of the knobs 35 and 34 are coincident with one another as shown in FIG. 3. In this manner, the auxiliary knob 34 can turn with respect to the rotating knob 35 in the range of play of the pins 20 in the elongated grooves 20'.

Figure 4:
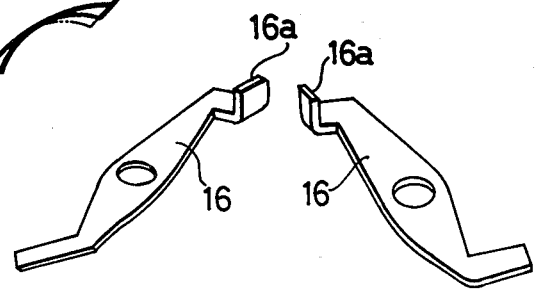
FIG. 4 is a perspective view showing one example of locking levers in the clutch mechanism.

A pair of locking levers 16 (FIG. 4) are pivotally mounted on supporting rods 17 at the rotational ends of the rotating plate 32, respectively, in such a manner that the pawls 16a and 16a of the locking levers confront each other. The rotating plate 32 is provided with iixing pins 18. Both ends of a spring 19 are in engagement with the fixing pins 18 and the other end of the lever 16 on each side of the knob 35. Hence the levers 16 are maintained biased inwardly with the other ends thereof abutting at all times against the pins 20 extending from the auxiliary knob 34.

A brake drum 31 is rotatably mounted on the cylindrical part of the rotating plate 32 mounted on the shaft 1a of the drum 1. The brake drum has an inside slidable contact surface 31a and an outside engaging tooth train 31b on its periphery. The pawls 16a of the locking levers 16 are maintained engaged with the teeth train 31b by the elastic forces of the springs, thus forming a clutch mechanism.

Figure 5:
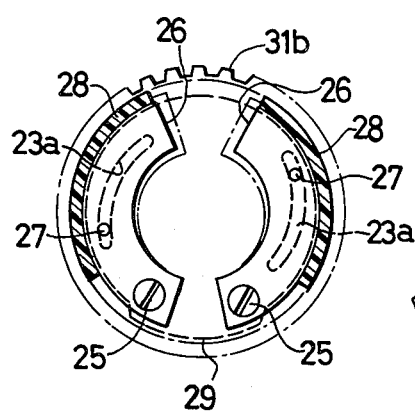
FIG. 5 is a plan view showing one example of a braking mechanism in the device according to the invention.

A stationary cylinder 2 fixedly secured to the stationary member 2a of the mechanism is fitted over the shaft 1a of the drum 1. A supporing plate 29 is fixedly secured to the stationary cylinder 2 by tightening a fixing member 30. First end portions of arcuate brake shoe plates 26 are pivotally mounted on supporting rods 25 fixedly secured to the supporting plate 29. This is shown in FIG. 5. Brake shoes 28 are secured to the outer wide walls which are provided at the rotable end portions of the plates 26 respectively, so that they are moved toward and away from the inside contact surface 31a of the drum 31 when turned.

A brake operating lever 8 is fixedly secured to a rotating pipe 4 which is fitted over aforementioned stationary cylinder 2. An operating plate 23 is secured to the pipe 4 with a fixing member 24. Guide grooves 23a and formed in the operating plate in such a manner that the distance between each guide grooves 23a and the center of the pipe is gradually changed. Pins 27 extending from the brake shoe plates 26 are slibably engaged with the guide groove 23a, respectively.

A mechanism for curving the top end part of the endoscope vertically is provided below the above-described mechanism for curving the top end part horizontally. The arrangement of the former mechanism is fundamentally similar to that of the latter mechanism. A rotating knob 22 for curving the top end part of the endoscope vertically and its auxiliary knob 12 for curving the top end part of the endoscope are rotatably mounted on a shaft 5a extending from a drum 5 with a fixing member 14 and a retaining member 11. A pulling string l₂ is wound on the drum 5. A brake drum 21 is rotatably fitted over the shaft 5a, in such a manner that its inside contact surface 21a confronts the above-described brake shoes 28 and is flush with the inside contact surface of the drum 31. That is, the brake shoes 28 acts on both of the brake drums.

The arrangement of the finger placing recesses of the knobs 22 and 12 is identical to that of the finger placing recesses of the knobs 34 and 35 described above. A clutch mechanism for the outside engaging teeth train 21b of the drum 21 is also similar to that as to the drum 31 in the horizontally curving mechanism, and therefore those components similar in functions are designated by like reference characters.

A second example of the device according to the invention utilizes the clutch mechanism between the rotating plate 32 and the brake drum 31, and its concerning mechanism in the above-described first example may be omitted. In this case, the rotating plate 32 and the brake drum 31 may be formed as a part of the rotating knob 35 or integral with the rotating knob 35.

The operation of the device according to the invention will be described. When the brake operating lever 8 is turned clockwise as viewed in FIG. 1 so that the rotating knobs 35 and 22 are braked, i.e., the top end part of the endoscope is held curved and the operating mechanism (for instance, the horizontal curving mechanism) is as indicated in FIGS. 2, 3 and 5.

In this operation, the operating plate 23 is turned clockwise as viewed in FIG. 5 through the rotating pipe 4 integral with the operating lever 8, and the positions of the guide grooves 23a are as indicated by the dotted lines in FIG. 5, that is, the pins 27 slidably engaged with the guide grooves 23a are positioned at the ends of the guide grooves 23, which are the furthest from the center of the rotating pipe 4. Accordingly, the brake shoe plates 26 connected to the pins 27 are turned around the respective supporting rods 25 so that their free ends are moved outwardly.

As a result, the brake shoes 28 on the brake shoe plates 26 abut against the inside contact surface 31 of the brake drum 31 to stop the brake drum, i.e., a braking force is applied to the brake drum 31.

The pawls 16a of the locking levers 16 are engaged at all times with the outside engaging tooth train 31b of the brake drum 31. Therefore, the drum 31 is fixedly coupled to the supporting plate 32 having the levers 16, i.e., the rotating knob 35 is fixedly coupled to the drum 1 having the pulling string l₁. If, under this condition, only the rotating knob 35 is turned, then it must be turned against the high friction force existing between the shoes 26 and the brake drum while turning the inside contact surface of the brake drum. Thus, this operation is suitable for finely adjusting the direction of the top end part of the endoscope.

In the case where it is required to significantly change the direction of the top end part of the endoscope under this braking condition, the operator holds both of the rotating knob 35 and the auxiliary knob 34 with his fingers to turn them as required. In this case, at the start of this operation the operator's fingers will hold the axiliary knob 34 earlier than the rotating knob 35 because the finger placing recesses 34a of the auxiliary knob are small in the amount of cut compared with the finger placing recesses 35a of the rotating knob, and accordingly the auxiliary knob 34 whose rotational load is less than that of the rotating knob 34 is turned earlier than the rotating knob 35.

If this turning operation is effectuated clockwise in FIG. 3, in the initial operation the auxiliary knob 34 is turned from the neutral position indicated by the dotted line to a position indicated by the one-dot chain line. In this operation, the pins 20 of the auxiliary knob 34 are moved along the elongated grooves 20'. As a result, the end of one locking lever 16 on the right side in FIG. 3 pivotally mounted on the rotating plate 32 is pushed clockwise in FIG. 3, and the lever 16 is turned clockwise around the supporting rod 17 against the elastic force of the spring 19. This is indicated by the dotted line in FIG. 3. Therefore, the pawl 16a of the lever 16 is disengaged from the outside engaging teeth train 31b of the brake drum 31, and the clutch coupling of the lever 16 is released. On the other hand, the pawl 16a of the other locking lever 16 on the left side in FIG. 3 causes no locking action in this rotation (clockwise in FIG. 3), i.e., the pawl 16a rides over the teeth train 31b, or the clutch mechanism is released. Therefore, the coupling condition between the drum 31 and the rotating knob 35 is released with respect to the clockwise direction. Thus, the operation can be freely accomplished with the brake released.

In the case where the knob is turned in the opposite direction (counterclockwise in FIG. 3), the operations of the pair of locking levers are opposite to those described above, so that the knob is also freely turned in this direction.

If after this preliminary operation, the auxiliary knob 34 is stopped, then the auxiliary knob 34 is automatically restored to its neutral position by the elastic forces of the spring 19, and simultaneously the locking levers 16 are engaged with the teeth train 31b. Accordingly, the direction of the top end part of the endoscope which has been changed by the operation is automatically maintained as it is.

The rotating knob 22 and its auxiliary knob 12 provided for changing the direction of the top end part of the endoscope vertically are operated in a manner similar to the above-described rotating knob 35 and auxiliary knob 34.

As is apparent from the above description, in changing the direction of the top end part of the endoscope, it is possible to selectively change the direction of the top end part of the endoscope vertically and horizontally under the braking action which has initially determined the direction of the top end part of the endoscope. That is, after the top end part of the endoscope has been orientated once, the direction of the top end part can be precisely adjusted. Therefore, in looking for a portion of the body cavity to be examined or in adjusting the position of the top end part for observation, the endoscope can be operated without extreme deviations of the top end part from its predetermined position.

It is obvious that if the brake operating lever 8 is turned counterclockwise as view in FIG. 1, then the operating plate 23 coupled to the brake operating lever 8 is turned counterclockwise. In this case, the pins 27 are moved to the ends of the guide grooves 23a, which are the closest to the center of the rotation. Simultaneously the brake shoe plates 26 are turned around the respective supporting rods 25 to the positions indicated by the two-dot chain lines in FIG. 5. As a result, the brake shoes 28 are disconnected from the brake drum 31; that is, the brake action is released, so that the operating mechanism can be freely operated.

In the device according to the invention, for the two independent curving mechanisms adapted to changing the direction of the top end part of the endoscope respectively vertically and horizontally, the brake drums turning with the operating knobs thereof are juxtaposed, and the brake shoes abut against and are removed from the brake drums by the external operation. More specifically, the brake shoes are positioned to abut against the brake drums remote from the axis of the operating knobs, and therefore stable braking frictional forces can be obtained. Furthermore, the vertically and horizontally curving mechanisms can be braked and the braking action can be released by operating only one external operating lever. Thus, the device according to the invention represents an improvement in practical use over the prior art.

Furthermore, according to the invention, the clutch mechanism is provided between the braking section and the rotating knob. The engagement and disengagement of the clutch mechanism can be achieved selectively by operating the rotating knob and the auxiliary knob provided near the rotating knob, or by operating only the rotating knob. The operation of the rotating knob only is very effective for finely adjusting the direction of the top end part of the endoscope because the operating knob is slidably opefated under the braking action. On the other hand, when the rotating knob and the auxiliary knob are operated, only the curving mechanism of the operating side can be operated as if it is free from the braking action. When the operation of the auxiliary knob is suspended, the braking action is automatically effectuated to maintain the condition of the curving mechanism. Accordingly, the invention is most effective as a braking mechanism for the endoscope of this type where the vertically curving mechanism and the horizontally curving mechanism are alternately operated.

Figure 6:
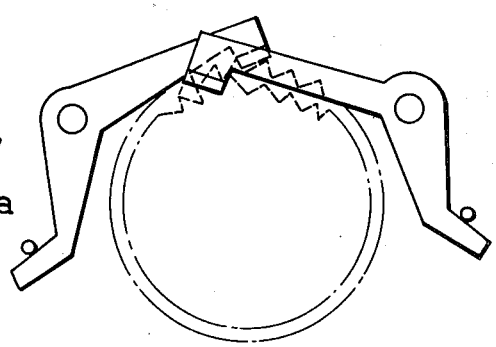
FIG. 6 is a plan view showing another example of the clutch mechanism in the device according to the invention.

A ratchet mechanism employing two trains of engaging teeth as shown in FIG. 6, or a conventional one-way engaging mechanism may be employed as the engaging mechanism of the clutch mechanism.

It is apparent that other modifications of the invention may be made without departing from its essential scope.

We claim:

1. In a device for changing a direction of end part of an endoscope in which a manual operating section is coupled to a top end part curving section through wires and said top end part curving section is curved vertically and horizontally by pulling said wires at said manual operating section, the improvement comprising:
   a pair of wires adapted to drive said top end part curving section vertically and horizontally, respectively;
   a pair of drive members for pulling said wires;
   rotating knobs integrally coupled to said pair of drive members to control said top end part curving section vertically and horizontally, respectively;
   a pair oi brake means
   a brake member mounted to a stationary member wherein said brake member is movable with respect to said pair of brake means; and
   an external operating lever for controlling the movement of said brake member, whereby said brake member abuts against said pair of brake means simultaneously by operating said external operating lever so that a vertically curving unit and a horizontally curving unit are simultaneously braked and in a braked condition either said vertically curving unit or said horizontally curving unit may be selectively actuated.

2. The device of claim 1 wherein said brake means are formed as a part of said rotating knobs.

3. The drive of claim 1 wherein said brake means comprise brake drum members clutched to said rotating knobs whereby said pair of brake drum members confront each other.

4. The device of claim 1 further comprising clutch mechanisms interposed between said rotating knobs and said brake means, said brake means comprising brake drums.

5. The device of claim 1 further cpmprising auxiliary knobs arranged adjacent to said rotating knobs whereby said auxiliary knobs are selectively operated simultaneously when said rotating knobs are operated.

6. In a device for changing a direction of the top end part of an endoscope in which a manual operating section is coupled to a top end part curving section through wires and said top end part curving section is curved vertically and horizontally by pulling said wires by said manual operating section, the improvement comprising:
a pair of wires adapted to drive said top end part curving section vertically and horizontally, respectively;
a pair of drive members for pulling said wires;
rotating knobs integrally coupled to said drive members;
brake means having brake drums, said brake means mounted coaxially with said rotating knobs, said brake means being normally rotatable;
frictional members adapted to abut against and retract from said brake means;
an external operating lever for controlling the abutting and retracting operations of said frictional members;
clutch mechanisms between said rotating knobs and said brake means; and
auxiliary knobs arranged adjacent to said rotating knobs, respectively, in such a manner that said auxiliary knobs are selectively operated simultaneously when said rotating knobs are operated;
and wherein said rotating knobs are normally coupled to said auxiliary knobs, means for disengaging said clutch mechanisms whereby said clutch mechanisms are released by selectively rotating said auxiliary knobs such that selective direction changing of the top end occurs.

7. The device of claims 1 or 6 wherein said wires are wrapped around said drive members and are directly driven by said drive members.

8. The device of claims 4 or 6 wherein said brake means have an inside slidable contact surface and a train of teeth on their outer periphery, and said clutch mechanism includes a pair of pivotally mounted locking levers each having pawl members thereon, said pawl members engaging said train of teeth and means to bias said pawls into engagement with said teeth.

9. The device of claims 4 or 6 further comprising an operating plate coupled to said operating lever, a plurality of grooves formed eccentrically in said operating plate, and pin members operably coupled to said brake drums and disposed in said grooves for varying the braking force as said external operating lever is actuated.

* * * * *